United States Patent
Ishikawa et al.

(10) Patent No.: US 8,263,222 B2
(45) Date of Patent: Sep. 11, 2012

(54) ORGANOSILICONE FINE PARTICLES, HAVING SPECIFIC SURFACE CHARACTERISTICS METHOD OF PRODUCING SAME, AND COSMETICS, RESIN COMPOSITIONS AND DEVELOPMENT TONERS CONTAINING SAME

(75) Inventors: Fumiyoshi Ishikawa, Aichi (JP); Mamoru Yasui, Aichi (JP); Chiaki Saito, Aichi (JP)

(73) Assignee: Takemoto Yushi Kabushiki Kaisha, Gamagori-shi, Aichi-ken (JP)

( * ) Notice: Subject to any disclaimer, the term of this patent is extended or adjusted under 35 U.S.C. 154(b) by 63 days.

(21) Appl. No.: 12/884,510

(22) Filed: Sep. 17, 2010

(65) Prior Publication Data

US 2011/0142893 A1  Jun. 16, 2011

Related U.S. Application Data

(63) Continuation of application No. PCT/JP2009/070884, filed on Dec. 15, 2009.

(51) Int. Cl.
| | |
|---|---|
| B32B 5/16 | (2006.01) |
| C08G 77/06 | (2006.01) |
| C08G 77/08 | (2006.01) |
| C08G 77/14 | (2006.01) |
| C08G 77/16 | (2006.01) |
| C08G 77/18 | (2006.01) |
| C08G 77/24 | (2006.01) |

(52) U.S. Cl. .................. 428/402; 106/287.16; 106/481; 428/447; 528/10; 528/31; 528/38; 528/42; 556/463; 556/465; 556/466; 556/476; 556/478

(58) Field of Classification Search .................. 428/402, 428/447; 528/10, 31, 38, 42; 556/463, 465, 556/466, 476, 478; 103/287.18, 481
See application file for complete search history.

(56) References Cited

U.S. PATENT DOCUMENTS

| 6,376,087 B1 * | 4/2002 | Ozeki et al. ................... 428/447 |
| 6,528,167 B2 | 3/2003 | O'Gara |
| 6,753,399 B2 * | 6/2004 | Inokuchi ......................... 528/14 |
| 7,393,911 B2 * | 7/2008 | Noda ............................. 528/10 |
| 7,704,517 B2 * | 4/2010 | Wang et al. ................... 424/401 |
| 2006/0089478 A1 * | 4/2006 | Noda ............................. 528/10 |

FOREIGN PATENT DOCUMENTS

| JP | 06-279589 | 10/1994 |
| JP | 09-059384 | 3/1997 |
| JP | 2000-191788 | 7/2000 |
| JP | 2000-345044 | 12/2000 |
| JP | 2003-171465 | 6/2003 |
| JP | 2006-089514 | 4/2006 |
| JP | 2006-117867 | 5/2006 |

OTHER PUBLICATIONS

WO patent application No. PCT/JP2009/070884, International Search Report mailed Mar. 16, 2010.

* cited by examiner

*Primary Examiner* — Hoa (Holly) Le
(74) *Attorney, Agent, or Firm* — Weaver Austin Villeneuve & Sampson LLP (57) ABSTRACT

Organosilicone fine particles of size in the range of 0.1-20 μm, each having 20 or more faces with indefinite shapes and a network of convex parts that surround these faces with indefinite shapes on its surface, and being spherical as a whole respond to highly advanced requirements of recent years including improvements in optical characteristics of resin compounds, usability and feeling of cosmetics and maintainability of fluidity of development toners. The invention further provides methods of producing such organosilicone fine particles.

5 Claims, 1 Drawing Sheet

ORGANOSILICONE FINE PARTICLES, HAVING SPECIFIC SURFACE CHARACTERISTICS METHOD OF PRODUCING SAME, AND COSMETICS, RESIN COMPOSITIONS AND DEVELOPMENT TONERS CONTAINING SAME

This application is a continuation of International Application No. PCT/JP2009/070884, filed Dec. 15, 2009.

BACKGROUND OF THE INVENTION

This invention relates to organosilicone fine particles, method of producing same, and cosmetics, resin compositions and development toners containing same. Fine particles of various substances have been in use in many applications. Their shapes are mostly indefinite, and fine particles of each type have been playing their suitable roles as an industrial material. In recent years, however, as the characteristics required of them in various applications become highly advanced, there are beginning to appear many situations where fine particles with controlled shapes are desired. As examples, improvements in the optical characteristics in the field of display devices and optical diffusers, miniaturization in size in the field of electronic components, improvements in usability and feeling in the field of cosmetics, and improvements in maintenance of fluidity related to the development characteristics of toners may be considered. This invention relates to organosilicone fine particles which can respond to such highly advanced requirements imposed on fine particles and more particularly to organosilicone fine particles having a plurality of faces having indefinite shapes and a network of convex parts surrounding the indefinitely shaped faces and being spherically shaped as a whole.

There have been many proposed ideas regarding both inorganic and organic fine particles with controlled shapes. As for organic fine particles, Japanese Patent Publications Tokkai 09-103804 and 11-292907, for example, considered polystyrene fine particles, Japanese Patent Publication Tokkai 11-116649, for example, considered polyurethane fine particles, Japanese Patent Publication Tokkai 11-140181, for example, considered polyimide fine particles, and Japanese Patent Publication Tokkai 61-159427, for example, considered organosilicone fine particles. Since almost all of these prior art organic fine particles are spherical or nearly spherical, there are in recent years an increasing number of situations wherein these prior fine particles cannot respond to the highly advanced requirements imposed upon them for purposes of use. In view of the above, as examples of organic fine particles with modified shapes, Japanese Patent Publication Tokkai 07-157672, for example, proposed hollow organic fine particles having large protrusions and indentations, Japanese Patent Publication Tokkai 2000-191788, for example, proposed organic fine particles having a plurality of small indentations on the surface, Japanese Patent Publication Tokkai 2003-171465, for example, proposed organic fine particles in shape of a rugby ball, and Japanese Patent Publication Tokkai 2003-128788, for example, proposed semispherical organic fine particles. Even such prior art organic fine particles with modified shapes have problems of not being able to fully respond to the highly advanced requirements of recent years imposed on them for purposes of use.

SUMMARY OF THE INVENTION

It is therefore an object of this invention to provide organosilicone fine particles which will be able to respond to the high advanced requirements of recent years imposed on them for purposes of actual use, including further improvements in optical characteristics such as total light transmittance and haze and in heat-resistance colorability related to resin compositions, further improvements in usability (extensions and expansions at the time of use) and in feeling (stickiness, roughness and durability) related to cosmetics, and further improvements in maintainability of fluidity related to development toners, as well as methods of producing and cosmetics, resin compositions and development toners containing such organosilicone fine particles.

The inventors herein have carried out investigations in order to solve the aforementioned problems and discovered as a result thereof that what are suitable are organosilicone fine particles of a specific kind having a plurality of faces (shown at 21 in FIGS. 1 and 2) having indefinite shapes on the surface and a network of convex parts (shown at 31 in FIGS. 1 and 2) surrounding these indefinitely shaped faces and being spherically shaped as a whole.

DETAILED DESCRIPTION OF THE INVENTION

This invention relates to organosilicone fine particles having a plurality of faces having indefinite shapes on the surface and a network of convex parts surrounding these indefinitely shaped faces and being spherically shaped as a whole, wherein the average value of the particle sizes $L_1$ is within the range of 0.1-20 µm each and each particle has at least 20 of such indefinitely shaped faces. In the above, the average value of the particle sizes is to be obtained from arbitrarily selected 20 particles from an image of the particles obtained by a scanning electron microscopic photograph, and the number of the faces on an observed particle is that counted on the scanning electron microscope photographic image multiplied by 2. This invention further relates to methods of producing and cosmetics, resin compositions and development toners containing such organosilicone fine particles.

Figure 1:
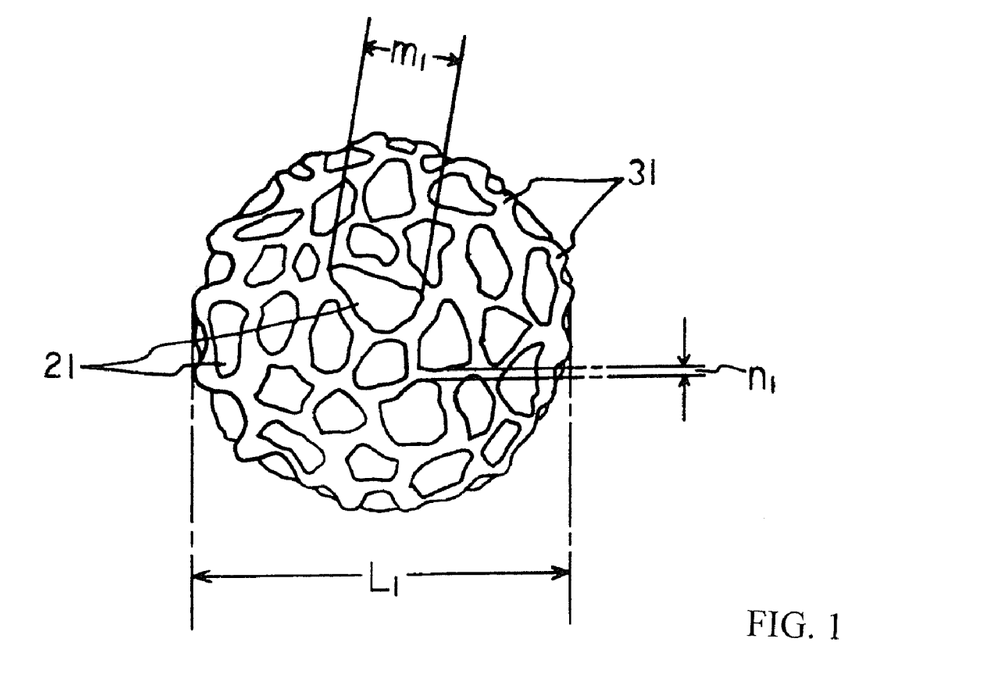
FIG. 1 is an approximate front view of an organosilicone fine particle embodying this invention.
Figure 2:
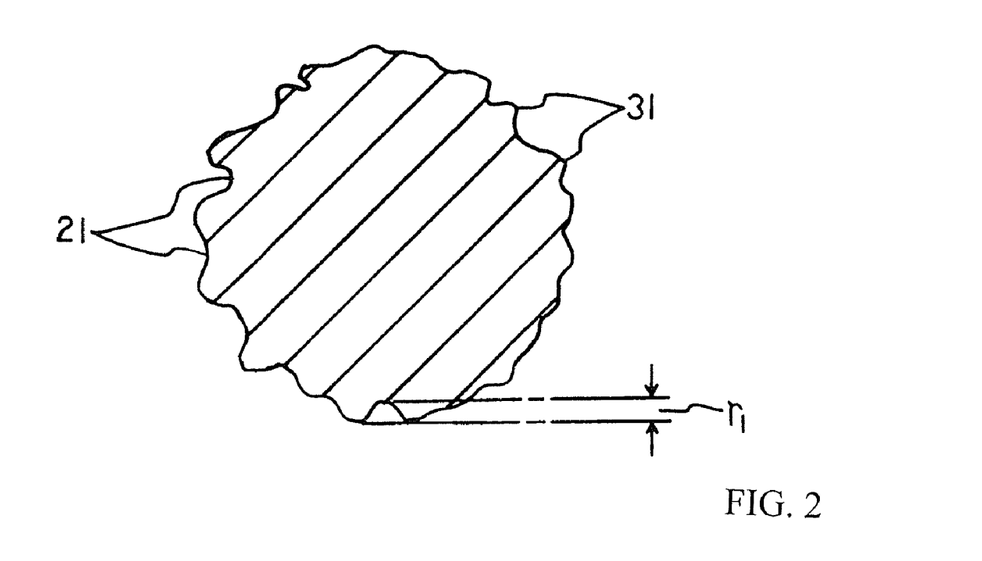
FIG. 2 is an approximate sectional view of an organosilicone fine particle embodying this invention.

Organosilicone fine particles according to this invention are explained first with reference to FIGS. 1 and 2. The organosilicone fine particles of this invention are characterized as having a plurality of faces having indefinite shapes on the surface and a network of convex parts surrounding these indefinitely shaped faces and being spherically shaped as a whole and satisfying the conditions as described above, that is, the average value of the particle sizes $L_1$ is within the range of 0.1-20 µm each, each particle has at least 20 of such indefinitely shaped faces, the average value of the particle sizes is to be obtained from arbitrarily selected 20 particles from an image obtained by a scanning electron microscopic photograph, and the number of the faces on an observed particle is that counted on a scanning electron microscope photographic image multiplied by 2.

Organosilicone fine particles of this invention have a plurality of faces 21 having indefinite shapes on their surfaces 11. There is no special limitation on the size of these faces 21 having indefinite shapes but it is preferable that 0.05≦(Average of the maximum sizes $m_1$ of the faces with indefinite shapes)/(Average of the sizes $L_1$ of the particles)≦0.5 where the average of the maximum sizes $m_1$ of the faces 21 is to be calculated from the maximum sizes $m_1$ of arbitrarily selected 20 particles observed in an image obtained by a scanning electron microscopic photograph.

On the surfaces of the organosilicone fine particles of this invention, the faces 21 having indefinite shapes are surrounded by a network of convex parts 31. There is no special limitation on the width of these convex parts 31 surrounding the faces 21 having indefinite shapes but it is preferable that $0.02 \leq$ (Average of the minimum width $n_1$ of the convex parts surrounding the faces having indefinite shapes)/(Average of the sizes $L_1$ of the particles)$\leq 0.1$ where the average of the minimum width $n_1$ of the convex parts surrounding the faces having indefinite shapes is to be calculated from the minimums of the widths of the convex parts 31 sandwiched between two mutually adjacent faces 21 having indefinite shapes on arbitrarily selected 20 of the organosilicone fine particles observed in an image obtained by a scanning electron microscopic photograph.

The network of convex parts 31 is at a higher position as seen from of the face 21 which is surrounded thereby. There is no special limitation on this height as seen from the face but it is preferable that $0.01 \leq$ (Average of maximum heights $r_1$ of the convex parts as seen from the surrounded face)/(Average of the sizes $L_1$ of the particles)$\leq 0.1$ where the average of maximum heights $r_1$ of the convex parts as seen from the surrounded face is to be calculated from the maximum heights $r_1$ of the convex parts as seen from the surrounded face on arbitrarily selected 20 of the organosilicone fine particles observed in an image obtained by a scanning electron microscopic photograph.

One of the useful characteristics of the organosilicone fine particles of this invention is the height of oil absorption. Although there is no special limitation on the oil absorption, it is preferable that it be in the range of 40-120 ml/100 g.

Organosilicone fine particles of this invention comprise a polysiloxane cross-linked structure with siloxane units forming a three-dimensional network structure. There is no special limitation on the kind and ratio of the siloxane units which form the polysiloxane cross-linked structure but those comprising siloxane units $SiO_2$, $R^1SiO_{1.5}$ and $R^2R^3SiO$ are preferred where $R^1$, $R^2$ and $R^3$ are each an alkyl group or a phenyl group with 1-4 carbon atoms such as methyl group, ethyl group, propyl group and butyl group but methyl group is preferable. Examples of siloxane units $R^1SiO_{1.5}$ and $R^2R^3SiO$ include methyl siloxane unit, ethyl siloxane unit, propyl siloxane unit, butyl siloxane unit and phenyl siloxane unit but methyl siloxane unit is preferable.

When the polysiloxane cross-linked structures for the organosilicone fine particles of this invention are formed with such siloxane units as described above, it is preferable that 15-35 molar % be siloxane units $SiO_2$, 55-75 molar % be siloxane units $R^1SiO_{1.5}$ and 10-20 molar % be siloxane units $R^2R^3SiO$ such that the total becomes 100 molar %.

Next, a method of producing organosilicone fine particles of this invention is described. Organosilicone fine particles of this invention may be produced as follows. Use is made of silanol group forming silicide $SiX_4$ at a rate of 15-35 molar %, silanol group forming silicide $R^4SiY_3$ at a rate of 55-75 molar %, and silanol group forming silicide $R^5R^6SiZ_2$ at a rate of 1-20 molar % such that the total becomes 100 molar % wherein $R^4$, $R^5$ and $R^6$ are each alkyl group with 1-4 carbon atoms or phenyl group and preferably methyl group, and X, Y and Z are each alkoxy group with 1-4 carbon atoms, alkoxyethoxy group having alkoxy group with 1-4 carbon atoms, acyloxy group with 2-4 carbon atoms, N,N-dialkylamino group having alkyl group with 1-4 carbon atoms, hydroxy group, halogen atom or hydrogen atom. Firstly, silanol group forming silicide $SiX_4$ is caused to contact water in the presence of an acidic catalyst to thereby generate silanol compound by undergoing hydrolysis. Next, this silanol compound thus generated is caused to undergo condensation reaction together with silanol group forming silicides $R^4SiY_3$ and $R^5R^6SiZ_2$ in an aqueous condition in the presence of an acidic catalyst and an amphoteric surfactant.

Silanol group forming silicide $SiX_4$ is a compound which results in forming siloxane units $SiO_2$. X is (1) alkoxy group with 1-4 carbon atoms such as methoxy group or ethoxy group; (2) alkoxyethoxy group having alkoxy group with 1-4 carbon atoms such as methoxyethoxy group and butoxyethoxy group; (3) acyloxy group with 2-4 carbon atoms such as acetoxy group and propyloxy group; (4) N,N-dialkylamino group having alkyl group with 1-4 carbon atoms such as dimethylamino group and diethylamino group; (5) hydroxy group; (6) halogen atom such as chlorine atom or bromine atom; or (7) hydrogen atom.

Specific examples of silanol group forming silicide $SiX_4$ include tetramethoxy silane, tetraethoxy silane, tetrabutoxy silane, trimethoxyethoxy silane, tributoxyethoxy silane, tributoxyethoxy silane, tetrapropyoxy silane, tetraacetoxy silane, tetra(dimethylamino) silane, tetra(diethylamino) silane, tetrahydroxy silane, chlorosilane triol, dichlorodisilanol, tetrachlorosilane and chlorotrihydrogen silane, among which tetramethoxy silane, tetraethoxy silane and tetrabutoxy silane are preferable.

Silanol group forming silicide $R^4SiY_3$ is a compound which results in forming siloxane units $R^1SiO_{1.5}$ where Y is similar to X described above and $R^4$ is similar to $R^1$ described above.

Specific examples of silanol group forming silicide $R^4SiY_3$ include methyltrimethoxy silane, ethyltriethoxy silane, propyltributoxy silane, butyltributoxy silane, phenyltrimethoxyethoxy silane, methyltributhoxyethoxy silane, methyltripropyoxy silane, methyltriacetoxy silane, methyl silane triol, methylchlorodisilanol, methyltrichloro silane, and methyltrihydrogen silane. Among the above, as explained above regarding $R^1$ in siloxane units $R^1SiO_{1.5}$, silanol group forming silicides which result in forming methyl siloxane unit, ethyl siloxane unit, propyl siloxane unit, butyl siloxane unit or phenyl siloxane unit are preferable and those that result in forming methyl siloxane unit are more preferable.

Silanol group forming silicide $R^5R^6SiZ_2$ is a compound which results in forming siloxane units $R^2R^3SiO$ where Z is similar to X described above and $R^5$ and $R^6$ are similar respectively to $R^2$ and $R^3$ described above.

Specific examples of silanol group forming silicide $R^5R^6SiZ_2$ include dimethyldimethoxy silane, diethyldiethoxy silane, dipropyldibutoxy silane, dibutyldimethoxy silane, methylphenylmethoxyethoxy silane, dimethylbutoxyethoxy silane, dimethyldiacetoxy silane, dimethyldipropyloxy silane, dimethodi(dimetholamino) silane, dimethyldi(diethylamino) silane, dimethyl silane diol, dimethylchloro silanol, dimethyldichloro silane, and dimethyldihydrogen silane. Among the above, as explained above regarding $R^2$ and $R^3$ in $R^2R^3SiO$, silanol group forming silicides which result in forming dimethyl siloxane unit, diethyl siloxane unit, dipropyl siloxane unit, dibutyl siloxane unit or methylphenyl siloxane unit are preferable and those that result in forming dimethyl siloxane unit are more preferable.

Organosilicone fine particles are produced by using silanol group forming silicide $SiX_4$ at a rate of 15-35 molar %, silanol group forming silicide $R^4SiY_3$ at a rate of 55-75 molar %, and silanol group forming silicide $R^5R^6SiZ_2$ at a rate of 1-20 molar % such that the total becomes 100 molar %. Firstly, silanol group forming silicide $SiX_4$ is caused to contact water in the presence of an acidic catalyst to thereby generate silanol compound by undergoing hydrolysis. Any conventionally known acidic catalyst for hydrolysis may be used. Examples of such acidic catalyst include inorganic acids such as hydrochloric acid, sulfuric acid, nitric acid and phosphoric acid and organic acids such as formic acid, acetic acid, methane sulfonic acid, toluene sulfonic acid, dodecylbenzene sulfonic acid, decyl sulfate, dodecyl sulfate, tetradecyl sulfate and hexadecyl sulfate. The amount of the catalyst at the time of hydrolysis is preferably 0.001-0.500% by mass of the total amount of the silanol group forming silicides that are being used.

Next, this silanol compound is caused to undergo condensation reaction together with silanol group forming silicides $R^4SiY_3$ and $R^5R^6SiZ_2$ in an aqueous condition in the presence of an acidic catalyst and an amphoteric surfactant. Any conventionally known acidic catalyst for this condensation process may be used, as was the case with the acidic catalyst for hydrolysis. The amount of the catalyst to be used for condensation is preferably 0.001-0.500% by mass of the total amount of the silanol group forming silicides that are being used.

Any conventionally known amphoteric surfactant may be added to the reacting system together with the acidic catalyst. Examples of such amphoteric surfactant includes betaine type amphoteric surfactants and alanine type amphoteric surfactants but betaine type amphoteric surfactants are preferable. Examples of such betaine type surfactant includes octyl dimethyl ammonio acetate, decyl dimethyl ammonio acetate, dodecyl dimethyl ammonio acetate, hexadecyl dimethyl ammonio acetate, octadecyl dimethyl ammonio acetate, nonadecyl dimethyl ammonio acetate, and octadecenyl dimethyl ammonio acetate. It is preferable to use the amphoteric surfactant at a rate of 0.001-0.550 mass % of the total amount of the silanol group forming silicides that are being used.

The mass ratio of water with respect to the total silanol group forming silicides that are being used is normally in the range of 10/90-70/30. The amount of the catalyst to be used varies, depending on its type and the kind of the silanol group forming silicide but it is usually less than 1 mass % of the total amount of the silanol group forming silicides being used and preferably 0.001-0.550 mass %. The reaction temperature is usually 0-40° C. but it is preferably less than 30° C. in order to avoid immediate condensation reaction of the silanol compounds generated by the hydrolysis.

According to this invention, organosilicone fine particles are produced through the hydrolysis and condensation reactions of silanol group forming silicides as described above. Since the catalysts for the hydrolysis can be used as the catalysis for the condensation reaction according to this invention, the reaction liquid containing silanol compounds generated by the hydrolysis can be directly used for the condensation reaction. A catalyst may further be added to this reaction liquid for the condensation reaction. Alternatively, the catalyst and the silanol compounds that have not reacted and remaining in the reaction liquid may be deactivated or removed before the reaction liquid is presented for the condensation reaction. The solid components of the organosilicone fine particles inside the aqueous suspension is generally adjusted to be 2-20 mass %, the amount of water is preferably adjusted such that this will become 5-15 mass %.

Organosilicone fine particles of this invention may be used as a water-containing material with the solid component adjusted to be 30-70% by being separated from the aqueous suspension of the reaction system after such hydrolysis and condensation reactions, say, by being passed through a metallic net, and being dehydrated by a centrifugal method or a pressure filtering method but they may also be used after being dried. A dried material may be obtained by the method of passing the aqueous suspension through a metallic net, dehydrating it by a centrifugal or pressure filtering method and drying it by heating at 100-250° C., by the method of drying it by heating the aqueous suspension in vacuum at 30-150° C. or by the method of directly drying the aqueous suspension by a spray dryer at 100-250° C. It is preferable to use such dried material after crushing it by means, for example, of a jet mill.

The organosilicone fine particles thus obtained are organosilicone fine particles having on their surface a plurality of faces 21 with indefinite shapes and a network of convex parts 31 surrounding these faces 21, being spherical as a whole, and satisfying the conditions described above.

Next, cosmetic articles according to this invention (hereinafter referred to as cosmetics of this invention) are described. The cosmetics of this invention are characterized as containing organosilicone fine particles of this invention at a rate of 0.1-10 mass %. The cosmetics of this invention make use of the superior optical characteristics and high oil absorption of the organosilicone fine particles of this invention. They are superior in their soft focus effect without roughness or glare, hiding effect against spots on the skin and spread on and contact to the body and effective against dropping of cosmetics due to sebum as they are used as a component of basic cosmetics in the liquid, cream or press form or make-up cosmetics.

Cosmetics of this invention are produced by appropriately using body pigment, white pigment, pearl pigment, colored pigment (dye), combining oil, water, surfactant, thickener, antiseptic, antioxidant, and perfume in addition to organosilicone fine particles of this invention. Cosmetics of this invention can be prepared by any conventionally known method of uniformly dispersing these components together with organosilicone fine particles of this invention.

Next, resin compositions according to this invention (hereinafter referred to as the resin compositions of this invention) are explained. The resin compositions of this invention are characterized as containing organosilicone fine particles of this invention at a rate of 0.1-10 mass %. The resin compositions of this invention are useful where there is a strong requirement for improved characteristics of resin composition having polymer materials as main component. For instruments for illumination and display devices, for example, there have been strong demands for superior resin compositions having high light transmittance and haze as well as superior heat-resistant colorability because of efficient utilization of light and highly advanced capabilities. The resin compositions of this invention are useful in such fields of application.

Finally, development toners according to this invention (hereinafter referred to as the development toners of this invention) are explained. The development toners of this invention are characterized as containing organosilicone fine particles of this invention at a rate of 0.1-10 mass %. The development toners of this invention serve to prevent separation from the toner surfaces by mixing an appropriate amount of organosilicone fine particles of this invention into the toner or the development agent so as to improve the maintainability of fluidity of the toner.

As explained above, the present invention has the favorable effect of providing new organosilicone fine particles which can respond to the highly advanced requirement for purposes of actual use such as further improving optical characteristics of resin compositions such as total light transmittance and haze, further improvements in usability and feeling in the case of cosmetics and further improvements in maintainability of fluidity in the case of development toners.

Examples are described in what follows in order to further explain the structure and effects of the present invention but it goes without saying that these examples are not intended to limit the scope of the invention. In the following description, "parts" will mean "mass parts" and "%" will mean "mass %".

TEST EXAMPLES

Part 1 (Synthesis of Organosilicone Fine Particles)

Test Example 1

Synthesis of Organosilicone Fine Particles (P-1)

Ion exchange water 2000 g was placed in a reactor vessel and dissolved by adding 30% aqueous solution of hydrochloric acid 0.09 g. Tetraethoxy silane 159.3 g (0.77 mols) was further added for hydrolysis at 15° C. for 60 minutes with stirring. In another reactor vessel, an aqueous solution having (carboxymethyl) dimethyl-3-[(1-oxododecyl)amino] propylammonium hydroxide 0.70 g and 30% aqueous solution of hydrochloric acid 2.70 g dissolved in ion exchange water 350 g was prepared and cooled to 10° C., and the aforementioned solution of hydrolysis product adjusted to the same temperature was gradually dropped into it. Methyltrimethoxy silane 338.7 g (2.49 mols) and dimethyldimethoxy silane 69.0 g (0.57 mols) were further added and it was left quietly for one hour with the temperature of the whole maintained at 13-15° C. After a condensation for 4 hours at the same temperature, the temperature was raised to 60° C. and a condensation reaction was carried out at this temperature for 5 hours to obtain a white suspension. After the white suspension was left quietly overnight, the liquid phase was removed by decantation to obtain a white solid phase. This white phase was washed with water by a usual method and dried to obtain organosilicone fine particles (P-1).

Organosilicone fine particles (P-1), thus obtained, were used to carry out observations and measurements by the use of a scanning electron microscope, measurements of oil absorption, elemental analyses, inductively coupled plasma spectroscopy analyses, FT-IR spectrum analyses and NMR spectrum analyses, as explained in detail below. Organosilicone fine particles (P-1) were organosilicone fine particles having on their surfaces a plurality of faces 21 with indefinite shapes and a network of convex parts 31 surrounding these faces 21 with indefinite shapes and being spherical as a whole, the average of their particle sizes $L_1$ being 2.6 μm and the number of the faces 21 with indefinite shapes per particle being 72. The average of the ratios (Average value of maximum sizes $m_1$ of faces 21 with indefinite shapes)/(Average value of particles sizes $L_1$) was 0.25, and the average of the ratio (Average of the minimum values of the width $n_1$ of the convex parts 31 in the network surrounding the faces 21 with indefinite shapes)/(Average value of the particle sizes $L_1$) was 0.056. The average of the ratios (Average of maximum values of the height $r_1$ of the convex parts 31 in the network as seen from the faces 31 with indefinite shapes)/(Average value of the particle sizes $L_1$) was 0.034. Organosilicone fine particles (P-1) were organosilicone fine particles comprising polysiloxane cross-link structures having siloxane units $SiO_2$ at a rate of 20 molar %, siloxane units $R^1SiO_{1.5}$ at a rate of 65 molar % and siloxane units $R^2R^3SiO$ at a rate of 15 molar % (the total being 100 molar %).

Observations and Measurements by a Scanning Electron Microscope

A scanning electron microscope (SEMEDX Type N (trade name) by HITACHI Co., Ltd,) was used to observe organosilicone fine particles (P-1) and to obtain SEM images at magnifications 2000-10000. Out of these images, 20 organosilicone fine particles (P-1) were arbitrarily extracted, their particle sizes $L_1$ were measured and their average was obtained. The number of the faces 21 with indefinite shapes per organosilicone fine particle was determined by the number of the faces 21 with indefinite shapes observed in the image multiplied by 2. The average value of the maximum size $m_1$ of the faces 21 with indefinite shapes was determined by obtaining the maximum size $m_1$ of each of 20 faces 21 with indefinite shapes arbitrarily extracted from the images and obtaining their average value. The average value of the minimum values of the width ($n_1$) of the convex parts in the network surrounding the faces 21 with indefinite shapes was determined by obtaining the minimum value of the width ($n_1$) of the 20 convex parts 31 arbitrarily extracted from the images sandwiched between mutually adjacent faces 21 with indefinite shapes and obtaining their average value. The maximum values $r_1$ of heights of the convex parts 31 in the network as seen from the faces 21 with indefinite shapes were obtained and their average value was determined.

Measurements of Oil Absorption by Organosilicone Fine Particles of this Invention Measurements were made according to JIS K5101-13-1: 2004.

Analysis of Siloxane Units Comprising Organosilicone Fine Particles

Organosilicone fine particles 5 g were accurately measured and added to 0.05N aqueous solution of sodium hydroxide 250 ml, and all of the hydrolysable groups in the organosilicone fine particles were extracted into the aqueous solution of sodium hydroxide. Organosilicone fine particles were separated from the extraction treatment liquid by ultracentrifugation, and after the separated organosilicone fine particles were washed with water, they were dried for 5 hours at 200° C. and used for elemental analyses, inductively coupled plasma spectroscopy analyses and FT-IR spectrum analyses for the measurement of total carbon content and total silicon content and for ascertaining silicon-carbon bonding and silicon-oxygen-silicon bonding. Proportions of siloxane units $SiO_2$ siloxane units $R^1SiO_{1.5}$ and siloxane units $R^2R^3SiO$ were calculated from the vales of these analyses, the NMR integration value of CP/MAS for solid $^{29}Si$, and the carbon numbers of $R^4$ of silanol group forming silicide $SiX_4$ and $R^5$ and $R^6$ of silanol group forming silicide $R^5R^6SiZ_2$.

Test Examples 2-7

Synthesis of Organosilicone Fine Particles (P-2)-(P-7)

Organosilicone fine particles (P-2)-(P-7) of Test Examples 2-7 were synthesized similarly to organosilicone fine particles (P-1) of Test Example 1 and observed, measured and analyzed as in Test Example 1.

Comparison Example 1

Synthesis of Organosilicone Fine Particles (R-1)

Ion exchange water 1080 g was placed in a reactor vessel and a uniform solution was obtained by adding acetic acid 0.2 g. Methyltrimethoxy silane 1788.8 g (8.6 mols) and tetraethoxy silane 190.4 g (1.4 mols) were further added, and hydrolysis was carried out by maintaining the temperature at 30° C. A transparent reaction liquid containing silanol compounds was obtained in about 30 minutes. Ion exchange water 475 g and dodecylbenzene sulfonic acid 50 g were placed in another reactor vessel and after they were sufficiently dissolved, the temperature was raised to 80-85° C. The aforementioned transparent reaction liquid 300 g was dropped into it over about 2 hours for carrying out a condensation reaction. After about 15 minutes of aging, this was gradually cooled and stirred for one hour until it reached a room temperature. After the end of the reaction, it was adjusted to pH7.0 with an aqueous solution of sodium carbonate and an aqueous suspension of organosilicone fine particles was obtained. White fine particles were filtered out from this aqueous suspension. The white fine particles were washed with water and dried for 3 hours at 150° C. with hot air to obtain organosilicone fine particles (R-1) 594 g. Organosilicone fine particles (R-1) were observed, measured and analyzed as in Test Example 1. Details of each example of organosilicone fine particles obtained above are summarized in Tables 1-3.

TABLE 2

| Kind of organo-silicone fine particles | Siloxane units $SiO_2$ Kind/Use rate (mol %) | Siloxane units $R^1SiO_{1.5}$ Kind/Use rate (mol %) | Siloxane units $R^2R^3SiO$ Kind/Use rate (mol %) | Shape as a whole |
|---|---|---|---|---|
| Test Ex. | | | | |
| 1 | P-1 | S-1/20 | S-2/65 | S-5/15 | *1 |
| 2 | P-2 | S-1/33 | S-2/57 | S-5/10 | *1 |
| 3 | P-3 | S-1/30 | S-2/55 S-3/5 | S-5/10 | *1 |
| 4 | P-4 | S-1/20 | S-2/59 S-4/6 | S-5/15 | *1 |
| 5 | P-5 | S-1/25 | S-2/55 | S-5/10 S-6/10 | *1 |
| 6 | P-6 | S-1/23 | S-2/47 S-4/12 | S-5/13 S-6/5 | *1 |
| 7 | P-7 | S-1/30 | S-2/51 S-3/9 | S-6/10 | *1 |
| Comp Ex. | | | | |
| 1 | R-1 | S-1/14 | S-2/86 | — | *2 |

In Table 2:
S-1: Silisic acid anhydrate unit
S-2: Methyl siloxane unit

TABLE 1

| | Kind of organo-silicone fine particles | Silanol group forming silicide $SiX_4$ Kind/Use rate (mol %) | Silanol group forming silicide $R^4SiY_3$ Kind/Use rate (mol %) | Silanol group forming silicide $R^5R^6SiZ_2$ Kind/Use rate (mol %) | Catalyst for hydrolysis Kind/Concentration (%) | Catalyst for condensation Kind/Concentration (%) | Surfactant Kind/Concentration (%) |
|---|---|---|---|---|---|---|---|
| Test Ex. | | | | | | | |
| 1 | P-1 | SM-1/20 | SM-3/65 | SM-6/15 | CA-1/0.017 | CA-1/0.143 | Z-1/0.124 |
| 2 | P-2 | SM-1/33 | SM-3/57 | SM-6/10 | CA-1/0.075 | CA-1/0.066 | Z-1/0.035 |
| 3 | P-3 | SM-1/30 | SM-3/55 SM-4/5 | SM-6/10 | CA-2/0.022 | CA-2/0.210 | Z-2/0.008 |
| 4 | P-4 | SM-2/20 | SM-3/59 SM-5/6 | SM-6/15 | CA-2/0.035 | CA-2/0.115 | Z-2/0.016 |
| 5 | P-5 | SM-2/25 | SM-3/55 | SM-6/10 SM-7/10 | CA-1/0.008 | CA-2/0.015 | Z-2/0.310 |
| 6 | P-6 | SM-2/23 | SM-3/47 SM-5/12 | SM-6/13 SM-7/5 | CA-2/0.030 | CA-1/0.011 | Z-1/0.025 |
| 7 | P-7 | SM-2/30 | SM-3/51 SM-4/9 | SM-7/10 | CA-1/0.400 | CA-2/0.020 | Z-1/0.025 |
| Comp Ex. | | | | | | | |
| 1 | R-1 | SM-1/14 | SM-3/86 | — | CA-2/0.010 | CA-3/25.763 | — |

In Table 1:
Test Ex.: Test Example
Comp Ex.: Comparison Example
Concentration: Mass % with respect to the total of silanol group forming silicides used
SM-1: Tetraethoxy silane
SM-2: Tetramethoxy silane
SM-3: Methyltrimethoxy silane
SM-4: Propyltrimethoxy silane
SM-5: Phenyltrimethoxy silane
SM-6: Dimethyldimethoxy silane
SM-7: Methylphenylmethoxyethoxy silane
CA-1: Hydrochloric acid
CA-2: Acetic acid
CA-3: Dodecylbenzene sulfonic acid
Z-1: 2-[3-(dodecanoylamino) propa-1-yl(dimethyl)aminio] acetate
Z-2: 3-[2-heptadeca-8-en-1-yl-1-(2-hydroxyethyl)-4,5-dihydro-1H-imidazol-1-ium-1-yl] propanoate TABLE 2-continued

| Kind of organo-silicone fine particles | Siloxane units $SiO_2$ Kind/ Use rate (mol %) | Siloxane units $R^1SiO_{1.5}$ Kind/ Use rate (mol %) | Siloxane units $R^2R^3SiO$ Kind/ Use rate (mol %) | Shape as a whole |
|---|---|---|---|---|

S-3: Propyl siloxane unit
S-4: Phenyl siloxane unit
S-5: Dimethyl siloxane unit
S-6: Methylphenyl siloxane unit
*1: Having on surface a plurality of faces 21 with indefinite shapes and a network of convex parts 31 surrounding the faces 21 with indefinite shapes and being spherical as a whole
*2: Having on surface a plurality of small approximately circular indentations and being spherical as a whole

TABLE 3

| | Kind of organo-silicone fine particles | Average value of $L_1$ (μm) | Number of faces 21 with indefinite shapes | (Average value of $m_1$)/(Average value of $L_1$) | (Average value of $n_1$)/(Average value of $L_1$) | (Average value of $r_1$)/(Average value of $L_1$) | Oil absorption (ml/100 g) |
|---|---|---|---|---|---|---|---|
| Test Ex. | | | | | | | |
| 1 | P-1 | 2.6 | 72 | 0.25 | 0.056 | 0.034 | 78 |
| 2 | P-2 | 3.9 | 68 | 0.20 | 0.062 | 0.051 | 71 |
| 3 | P-3 | 17.1 | 120 | 0.13 | 0.065 | 0.045 | 102 |
| 4 | P-4 | 0.5 | 32 | 0.15 | 0.076 | 0.081 | 65 |
| 5 | P-5 | 12.8 | 38 | 0.28 | 0.036 | 0.019 | 68 |
| 6 | P-6 | 7.5 | 28 | 0.39 | 0.083 | 0.027 | 65 |
| 7 | P-7 | 0.8 | 24 | 0.22 | 0.095 | 0.076 | 62 |
| Comp Ex. | | | | | | | |
| 1 | R-1 | 2.8 | 36 | 0.05 | 0.217 | 0.023 | 57 |

In Table 3:
Average value of $L_1$: Average value of particle sizes $L_1$ regarding arbitrarily selected 20 organosilicone fine particles
Average value of $m_1$: Average value of maximum sizes $m_1$ of faces 21 with indefinite shapes regarding arbitrarily selected 20 organosilicone fine particles
Average value of $n_1$: Average value of minimum widths $n_1$ of convex parts 31 surrounding a face 21 with indefinite shape regarding arbitrarily selected 20 organosilicone fine particles
Average value of $r_1$: Average value of highest values $r_1$ of height of convex part in a network as seen from the faces 21 with indefinite shapes regarding arbitrarily selected 20 organosilicone fine particles Part 2 (Preparation and Evaluation of Foundations)

After organosilicone fine particles for comparison have been prepared, foundations were prepared by using the organosilicone fine particles shown in Table 5 and evaluated.
Synthesis of Organosilicone Fine Particles (R-2)

Ion exchange water 526 g, 25 mass % ammonia water 1.6 g and methanol 118 parts were placed inside a four-mouth flask and 2-(3,4-epoxy cyclohexyl)ethyltrimethoxy silane 30 g was added through a mouth while stirring to prepare an emulsion of organosilicone fine particles by their hydrolysis and condensation reactions. The preparation time for this emulsion was 2 hours from the beginning of the hydrolysis and condensation reactions. A portion of the prepared emulsion was collected, and the average size of the organosilicone fine particles as measured by COULTER MULTISIZER (trade name) produced by BECKMAN COULTER was 2.02 μm. Separately, a monomer emulsion was prepared by adding styrene 60 g as monofunctional monomer, dipentaerystol hexaacrylate 40 g as multifunctional monomer and 2-2'-azo-bis (2,4-dimethyl valeronitrile) (V-65 (trade name) produced by Wako Pure Chemical Industries Co., Ltd.) 2 g as cross-linking reagent to an emulsifier solution prepared with poly (oxy-1,2-ethaanediyl)-α-sulfo-ω-[bis(1-phenylethy)phe-noxy]-ammonium salt (HITENOL NF-08 (trade name) produced by Dai-ichi Kogyo Seiyaku Co., Ltd.) 2.5 g and ion exchange water 175 g, and processing with a homomixer under the conditions of 6000 rpm and 5 minutes. The aforementioned emulsion liquid was then mixed with this monomer emulsion and stirred. A portion of the liquid mixture was collected two hours after the monomer emulsion was mixed and observed with a microscope. It was found that the organosilicone fine particles have absorbed the components of the monomer emulsion and been swollen. Next, after the temperature of the liquid mixture of the monomer emulsion and the emulsion liquid was raised to 65° C. in the nitrogen atmosphere, the monomers absorbed by the organosilicone fine particles were caused to undergo radical polymerization by maintaining this temperature for 2 hours. Finally, the cake obtained by separation of solid from liquid from the liquid after the radical polymerization was washed with ethanol and dried for 12 hours at 80° C. to obtain organosilicone fine particles (R-2). Organosilicone fine particles (R-2) thus obtained were observed and measured as in Part 1 and it could be ascertained that their average size was 3.5 μm and that a plurality of indentations with irregular shapes were present on their surfaces.

Preparation of Foundations

Pigments numbered 1-7 in Table 4 were mixed by using a mixer in the ratios shown also in Table 4. Separately, components numbered 8-12 in Table 4 were collected in the ratios shown also in Table 4 and what was obtained by heating them to 40° C. and mixed together was added into the aforementioned mixture obtained by the mixer to obtain a final mixture. After the final mixture thus obtained was left to be cooled, it was crushed and formed to prepare a foundation.

TABLE 4

| Number | Component | Mixing ratio (mass %) |
|---|---|---|
| 1 | Object particles for evaluation | 7 |
| 2 | Titanium oxide | 10 |
| 3 | Talc | 20 |
| 4 | Sericite | 35 |
| 5 | Red iron oxide | 0.45 |
| 6 | Yellow iron oxide | 1 |
| 7 | Black iron oxide | 0.05 |

TABLE 4-continued

| Number | Component | Mixing ratio (mass %) |
|---|---|---|
| 8 | Fluidic paraffin | 10 |
| 9 | Octylmethyl cyclotetra siloxane | 5 |
| 10 | Polyoxy alkylene modified ester | 1.5 |
| 11 | Sorbitan aliphatic acid ester | 5 |
| 12 | Myristyl alcohol | 5 |

Evaluation of Foundations

The aforementioned sample was evaluated as follows by 20 female panel members regarding its usability (extension and expansion at the time of use) and feeling (stickiness, roughness and durability):

5: Very good
4: Good
3: Ordinary
2: Slightly bad
1: Bad

The average of the results is shown in Table 5 by rounding off to the nearest whole number.

TABLE 5

| | Kind of organosilicone fine particles | Evaluation | | | |
|---|---|---|---|---|---|
| | | Extension and expansion | Stickiness | Roughness | Durability |
| Test Example | | | | | |
| 8 | P-1 | 5 | 5 | 5 | 5 |
| 9 | P-2 | 5 | 5 | 5 | 5 |
| 10 | P-3 | 4 | 5 | 5 | 4 |
| 11 | P-4 | 5 | 4 | 5 | 4 |
| 12 | P-5 | 5 | 4 | 4 | 4 |
| 13 | P-6 | 4 | 5 | 4 | 4 |
| 14 | P-7 | 4 | 4 | 4 | 4 |
| Comp. Example | | | | | |
| 2 | R-1 | 4 | 3 | 4 | 3 |
| 3 | R-2 | 3 | 2 | 2 | 3 |
| 4 | R-3 | 2 | 2 | 2 | 3 |
| 5 | R-4 | 2 | 2 | 2 | 2 |
| 6 | R-5 | 1 | 1 | 1 | 1 |

In Table 5:
R-3: Spherical silicone fine particles (Tospearl (trade name) produced by TOSHIBA silicone Co., Ltd)
R-4: Spherical vinyl fine particles (Ganz pearl GSM1261 (trade name) produced by Ganz Chemical Co., Ltd.)
R-5: Talc As shown clearly in Table 5, organosilicone fine particles of this invention, when used in cosmetics, exhibit superior effects in terms of usability and feeling.

Part 3 (Preparation and Evaluation of Polycarbonate Resin Compositions)

Organosilicone fine particles of the examples shown in Table 6 were used as follows to prepare polycarbonate resin compositions and evaluated.

Preparation of Polycarbonate Resin Compositions

After organosilicone fine particles shown in Table 2 (0.7 parts) were added to polycarbonate resin (Panlite K1285 (trade name) produced by Teijin Chemicals, Ltd.) (100 parts) and mixed together, a biaxial extruder (40 mmΦ) equipped with vent was used to melt and mix at resin temperature of 280° C., and extrusion was carried out to produce pellets as polycarbonate resin compositions. These pellets were provided to an injection forming device, and sample plates with thickness 3 mm and width 200 mm were obtained by forming at cylinder temperature of 230° C. and mold temperature of 60° C.

Evaluation of Polycarbonate Resin Compositions

The aforementioned sample plates produced by using the pellets as polycarbonate resin compositions were used as explained below not only to measure total light transmittance and haze but also to obtain heat-resistant colorability. The results are shown in Table 6.

Total Light Transmittance and Haze

Measurements were made according to JIS-K7105 (1981) by using NDH-2000 (trade name) produced by Nippon Denshoku Industries Co., Ltd.

Heat-Resistant Colorability

The sample plates were placed inside a hot-air circulating oven at temperature of 80° C. and kept for 180 minutes. The b-value as the degree of coloring of the sample plates before and after this heating process was measured by using a color meter (CR-300 (trade name) produced by Minolta Co., Ltd.) and shown in terms of the color index, according to JIS-Z8729 (2004) and Δb was calculated according to the formula:

$$\Delta b = b^2 - b^1$$

where $b^1$ is the value of b of the sample plate before the heating process and $b^2$ is the value of b of the sample plate after the heating process.

TABLE 6

| | Type of organosilicone find particles | Total light transmittance (%) | Haze | Heat-resistant colorability |
|---|---|---|---|---|
| Test Example | | | | |
| 15 | P-1 | 93.1 | 89.8 | 0 |
| 16 | P-2 | 92.8 | 90.1 | 0 |
| 17 | P-3 | 88.7 | 87.1 | 0.1 |
| 18 | P-4 | 87.4 | 86.5 | 0.2 |
| 19 | P-5 | 86.3 | 86.1 | 0.2 |
| 20 | P-6 | 85.1 | 85.9 | 0.2 |
| 21 | P-7 | 84.3 | 85.5 | 0.3 |
| Comparison Example | | | | |
| 6 | R-1 | 82.1 | 84.3 | 0 |
| 7 | R-2 | 81.5 | 83.2 | 2.2 |
| 8 | R-3 | 81.1 | 82.3 | 0.1 |
| 9 | R-4 | 81.2 | 80.2 | 3.6 |
| 10 | R-6 | 78.4 | 78.8 | 0.5 |

In Table 6:
R-6: Calcium carbonate
Total light transmittance: %
Heat-resistant colorability: Value of Δb As shown clearly in Table 6, organosilicone fine particles of this invention, when used in a resin composition, exhibit superior effects in terms of total light transmittance, haze and heat-resistance colorability.

Part 4 (Preparation and Evaluation of Development Toners)

Development toners were prepared by using organosilicone fine particles of the examples shown in Table 7 and evaluated as follows.

Preparation of Development Toners

Development toners were prepared by steps (1)-(12) shown below.

(1) Preparation of Fine Particle Dispersion Liquids

Water 683 g, sodium polyoxyethylene methacryloyl sulfate (ELEMINOL RS-30 (trade name) produced by SANYO CHEMICAL INDUSTRIES CO., LTD.) 11 g, styrene 83 g, methacrylic acid 83 g, butyl acrylate 110 g an ammonium persulfate 1 g were placed in a reactor vessel and stirred for 15 minutes at 400 rpm to obtain a white emulsion. It was heated to raise the system temperature to 75° C. and allowed to react for 5 hours. A 1% aqueous solution of ammonium persulfate 30 g was further added for aging at 75° C. for 5 hours to obtain an aqueous dispersion (fine particle dispersion 1) of vinyl resin (copolymer of styrene-methacrylic acid-butyl acrylate-sodium polyoxyethylene methacryloyl sulfate). The weight average particle size of this fine particle dispersion 1 was 105 nm. When a portion of this fine particle dispersion 1 was dried and separated singly, the glass transition temperature of this resin part was 59° C. and its weight average molecular weight was 150,000.

(2) Preparation of Water Phase

Water 990 g, 83 g of aforementioned fine particle dispersion liquid 1, a 48.5% aqueous solution of disodium dodecyl diphenyl ether disulfonate (ELEMINOL MON-7) 37 g and ethyl acetate 90 g were mixed and stirred to obtain a milky-white liquid. This is referred to as water phase 1.

(3) Synthesis of Low Molecular Weight Polyester

Bisphenol A ethylene oxide 2 mol addition 229 g, bisphenol A propylene oxide 3 mol addition 529 g, terephthalic acid 208 g, adipic acid 46 g and dibutyl tin oxide 2 g were placed in a reactor vessel and reacted for 8 hours under normal pressure at 230° C. After a reaction under a reduced-pressure condition of 10-15 mmHg for 5 hours, trimellitic anhydride 44 g was added and reacted under a reduced-pressure condition for 2 hours at 180° C. to obtain low molecular weight polyester 1. This was found to have number average molecular weight of 2500, weight average molecular weight of 6700, glass transition temperature of 43° C., and acid value of 25.

(4) Synthesis of Intermediate Polyester and Prepolymer

Intermediate polyester was obtained by placing bisphenol A ethylene oxide 2 mol addition 682 g, bisphenol A propylene oxide 2 mol addition 81 g, terephthalic acid 283 g, trimellic anhydride 22 g and dibutyl tin oxide 2 g in a reactor vessel to react under normal pressure for 8 hours at 230° C. and further under a reduced-pressure condition of 10-15 mmHg for 5 hours. This was found to have number average molecular weight of 2100, weight average molecular weight of 9500, glass transition temperature of 55° C., acid value of 0.5 and hydroxyl value of 51. Prepolymer 1 was further obtained by placing 410 g of this intermediate polyester 1, isophorone diisocyanate 89 g and ethyl acetate 500 g in another reactor vessel and reacting for 5 hours at 100° C. The free isocyanate mass % of this prepolymer 1 was 1.53%

(5) Synthesis of Ketimine

Ketimine compound 1 was obtained by placing isophorone diamine 170 g and methylethyl ketone 75 g and reacting for 5 hours at 50° C. The amine value of this ketimine compound was 418.

(6) Production of Master Batch

Master batch 1 was obtained by mixing water 35 g, phthalocyanine pigment (FG7351 (trade name) produced by TOYO INK MFG. Co. Ltd.) 40 g, and polyester resin (RS801 (trade name) produced by SANYO CHEMICAL INDUSTRIES Co., Ltd.) 60 g by means of a Henschel mixer and, after the mixture was mixed by using two rollers for 30 minutes at 150° C., rolling, cooling and crushing this mixture with a pulverizer.

(7) Preparation of Pigment-Wax Dispersion

After 378 g of aforementioned low molecular weight polyester 1, Carnauba wax 110 g, CCA (salicylic acid metal complex E-84 produced by ORIENT CHEMICAL INDUSTRIES Co., Ltd.) 22 g and ethyl acetate 947 g were placed in a vessel and the temperature was raised to 80° C. while stirring and kept at 80° C. for 5 hours, they were cooled over one hour to 30° C. Ingredient solution 1 was obtained by placing 500 g of aforementioned master batch 1 and ethyl acetate 500 g in another vessel and mixing them for one hour. Next, 1324 g of this ingredient solution 1 was shifted into another vessel and carbon black and wax were dispersed by using a bead mill (Ultraviscomill (trade name) produced by AIMEX Co., Ltd.) under the condition of inflow speed=1 kg/hour, peripheral speed of disk=6 m/second, 0.5 mm zirconia beads filled at 80 volume %, and 3 passes. Next, 1324 g of 65% ethyl acetate solution of aforementioned low molecular weight polyester 1 was added to obtain pigment-wax dispersion 1 by one pass of the bead mill under the same conditions as described above. The solid concentration (130° C., 30 minutes) of this pigment-wax dispersion 1 was 50%.

(8) Preparation of Emulsified Slurry

Emulsified slurry 1 was obtained by placing 648 g of aforementioned pigment-wax dispersion 1, 154 g of aforementioned prepolymer 1 and 6.6 g of aforementioned ketimine compound 1 in a vessel to mix them with a homomixer for one minute at 5000 rpn and thereafter adding 1200 g of aforementioned water phase 1 thereto and further mixing them together with a homomixer for 20 minutes at 13000 rpm.

(9) Preparation of Shape-Controlling Slurry

Shape-controlling slurry 1 was obtained by adding aforementioned emulsified slurry 1 into an aqueous solution obtained by placing ion exchange water, an activating reagent and a thickener at appropriate ratios in a vessel and stirring together and mixing them together for one hour with a homomixer at 2000 rpm.

(10) Preparation of Dispersion Slurry

Dispersion slurry 1 was obtained by placing aforementioned shape-controlling slurry in a vessel, removing solvent for 8 hours at 30° C., and thereafter aging for 4 hours at 45° C.

(11) Preparation of Toner Parent Particles

Toner parent particles A were obtained by filtering 100 g of aforementioned dispersion slurry at a reduced pressure and thereafter carrying out washing and drying as follows:

(i) Ion exchange water 100 g was added to a filtered cake and they were mixed for 10 minutes by a homomixer at 12000 rpm and thereafter filtered.

(ii) A 10% aqueous solution of sodium hydroxide 100 g was added to the filtered cake of (i) and they were mixed for 30 minutes by a homomixer at 12000 rpm and thereafter filtered at a reduced pressure.

(iii) 10% hydrochloric acid 100 g was added to the filtered cake of (ii) and they were mixed for 10 minutes by a homomixer at 12000 rpm and thereafter filtered.

(iv) Ion exchange water 300 g was added to the filtered cake of (iii) and after they were mixed for 10 minutes by a homomixer at 12000 rpm, they were filtered twice to obtain filtered cake 1. This filtered cake 1 was dried with an air-circulating drier for 48 hours at 45° C., shifted through a mesh with openings of 75 μm to obtain final toner parent particles A.

(12) Preparation of Development Toners

Development toners were obtained by adding each example of organosilicone fine particles shown in Table 7 into aforementioned toner parent particles A at a rate of 1.0%, mixing them by a Henschel mixer such that the peripheral speed of its stirring fins will be 20 m/s, thereafter mixing thereto 0.8 g of hydrophobic titanium oxide with average particle size of 15 nm treated or covered with isobutyl and 1.0 g of hydrophobic silica with average particle size of 12 nm treated or covered with hexamethyldisilazane by a Henschel mixer such that the peripheral speed of its stirring fins will be 20 m/s.

Evaluation of Development Toners

Maintainability of fluidity of each example of development toners shown in Table 7 was evaluated as follows. Firstly, fluidity of development toners immediately after their preparation is measured by means of POWDER TESTER PT-S (trade name) produced by HOSOKAWA MICRON Corporation and the value obtained is defined as X. Next, 10 g of development toners immediately after their preparation and 20 g of iron powder carrier with no surface coating and having average volume size of 50 μm are mixed together, sealed in a 50 ml glass vial tube and provided to ROCKING MILL (trade name) produced by SEIWA GIKEN Corporation, providing forced oscillations at maximum oscillation amplitudes. After 30 minutes, development toners and iron powder carrier were separated by a 25-micron sieve. Fluidity of the development toners thus separated is similarly measured by the same POWDER TESTER PT-S and the value obtained is defined as Y. Maintainability of fluidity was calculated as $(1-|(X-Y)/X|) \times 100$ and evaluated as follows:

AA: Maintainability of fluidity was 85 or greater

A: Maintainability of fluidity was 75 or greater but less than 85

B: Maintainability of fluidity was 65 or greater but less than 75

C: Maintainability of fluidity was less than 65

The results of evaluation are shown in Table 7.

TABLE 7

| | Kind of organosilicone fine particles | Maintainability of fluidity |
|---|---|---|
| Test Example | | |
| 22 | P-1 | AA |
| 23 | P-2 | AA |
| 24 | P-3 | A |
| 25 | P-4 | A |
| 26 | P-5 | A |
| 27 | P-6 | A |
| 28 | P-7 | A |
| Comparison Example | | |
| 11 | R-1 | B |
| 12 | R-2 | B |
| 13 | R-3 | B |
| 14 | R-4 | B |
| 15 | R-6 | C |

As shown clearly in Table 7, organosilicone fine particles of this invention, when used for the production of development toners, exhibit superior effects for maintainability of their fluidity.

What is claimed is:

1. Organosilicone fine particles each having 20 or more faces with indefinite shapes and a network of convex parts that surround said faces with indefinite shapes on its surface, and being spherical as a whole; said organosilicone fine particles having oil absorption of 40-120 ml/100 g and comprising a polysiloxane cross-linked structures with siloxane units $SiO_2$ at a rate of 15-35 molar %, siloxane units $R^1SiO_{1.5}$ at a rate of 55-75 molar %, and siloxane units $R^2R^3SiO$ at a rate of 1-20 molar % such that the total is 100 molar %, where $R^1$, $R^2$ and $R^3$ are each alkyl group with 1-4 carbon atoms or phenyl group;

wherein said particles have an average particle size in the range of 0.1-20 μm, said average particle size being an average value obtained from 20 arbitrarily selected particles on a scanning electron microscope image of said particles, and the number of faces with indefinite shapes per particle is the observed number of faces with indefinite shapes on the particle on a scanning electron microscope image of said particles multiplied by 2;

wherein said faces with indefinite shapes have an average maximum size value which is an average value calculated from the maximum size of the faces with indefinite shapes of 20 of said organosilicone fine particles arbitrarily selected from a scanning electron microscope image of said particles, and wherein $0.05 \leq$ (said average maximum size value)/(said average particle size) $\leq 0.5$;

wherein said convex parts surrounding said faces with indefinite shapes have an average minimum width value calculated from the minimum widths of convex parts sandwiched by two mutually adjacent faces with indefinite shapes 20 of said particles arbitrarily selected from a scanning electron microscope image of said particles, and wherein $0.02 \leq$ (said average minimum width value)/(said average particle size) $\leq 0.1$; and wherein said network of convex parts has an average maximum height value calculated from maximum values of heights of the networks of convex parts as seen from the faces with indefinite shapes of 20 of said organosilicone fine particles arbitrarily selected from a scanning electron microscope image of said particles, and wherein $0.01 \leq$ (said average maximum height value)/(said average particle size) $\leq 0.1$.

2. A method of producing organosilicone fine particles of claim 1, said method comprising the steps of generating silanol compound by using silanol group forming silicide $SiX_4$ at a rate of 15-35 molar %, silanol group forming silicide $R^4SiY_3$ at a rate of 55-75 molar %, and silanol group forming silicide $R^5R^6SiZ_2$ at a rate of 1-20 molar % such that the total is 100 molar % to thereby cause silanol group forming silicide $SiX_4$ to undergo hydrolysis by contacting water in the presence of an acidic catalyst, and causing said silanol compound to undergo a condensation reaction with silanol group forming silicide $R^4SiY_3$ and silanol group forming silicide $R^5R^6SiZ_2$ in an aqueous condition in the presence of an acidic catalyst and an amphoteric surfactant, where $R^4$, $R^5$ and $R^6$ are each alkyl group with 1-4 carbon atoms or phenyl group, and X, Y and Z are each alkoxy group with 1-4 carbon atoms, alkoxyethoxy group having alkoxy group with 1-4 carbon atoms, acyloxy group with 2-4 carbon atoms, N,N-dialkylamino group having alkyl group with 1-4 carbon atoms, hydroxy group, halogen atom or hydrogen atom.

3. Cosmetics including organosilicone fine particles of claim 1 at a rate of 0.1-10 mass %.

4. A resin composition including organosilicone fine particles of claim 1 at a rate of 0.1-10 mass %.

5. A development toner including organosilicone fine particles of claim 1 at a rate of 0.1-10 mass %.

* * * * *